United States Patent [19]

Ruppersberger et al.

[11] Patent Number: 5,242,685
[45] Date of Patent: Sep. 7, 1993

[54] COPPER-CONTAINING AGENT FOR CONTROLLING FUNGI AND BACTERIA

[75] Inventors: Karl-Georg Ruppersberger, Weisenheim; Gregor Ley, Wattenheim, both of Fed. Rep. of Germany

[73] Assignee: BASF Aktiengesellschaft, Ludwigshafen, Fed. Rep. of Germany

[21] Appl. No.: 767,536

[22] Filed: Sep. 27, 1991

Related U.S. Application Data

[63] Continuation of Ser. No. 273,727, Nov. 18, 1988, abandoned, which is a continuation of Ser. No. 26,436, Mar. 16, 1987, abandoned.

Foreign Application Priority Data

Mar. 15, 1986 [DE] Fed. Rep. of Germany ....... 3608681

[51] Int. Cl.$^5$ .................. A01N 59/20; A61K 31/74
[52] U.S. Cl. ................. 424/78.26; 424/630; 424/635; 525/330.2
[58] Field of Search ............. 424/81, 78.26, 630, 424/635; 426/78.08; 525/330.2

[56] References Cited

U.S. PATENT DOCUMENTS

| | | | |
|---|---|---|---|
| 4,175,090 | 11/1979 | Berry ........................... | 260/438.1 |
| 4,409,358 | 10/1983 | Kraft et al. .................. | 524/547 |
| 4,566,997 | 1/1986 | Sato ............................ | 260/105 |

FOREIGN PATENT DOCUMENTS

| | | |
|---|---|---|
| 970321 | 1/1951 | European Pat. Off. . |
| 0039538 | 11/1981 | European Pat. Off. . |
| 0039788 | 10/1981 | Fed. Rep. of Germany . |

*Primary Examiner*—Peter F. Kulkosky
*Attorney, Agent, or Firm*—Oblon, Spivak, McClelland, Maier & Neustadt

[57] ABSTRACT

Agents for controlling fungi or bacteria, based on an aqueous solution which contains a polycarboxylic acid, ammonia and more than 10% of copper, and a process for their preparation.

7 Claims, No Drawings

COPPER-CONTAINING AGENT FOR CONTROLLING FUNGI AND BACTERIA

This application is a continuation of Ser. No. 07/273,727, filed on Nov. 18, 1988, now abandoned, which is a continuation of Ser. No. 07/026,436, filed Mar. 16, 1987, now abandoned.

The present invention relates to a copper-containing crop protection agent in the form of an aqueous solution which contains a polycarboxylic acid, ammonia and more than 10% by weight of copper.

It has been disclosed that an agent which contains a copper ammine salt of a polycarboxylic acid containing from 60 to 100% of acrylic acid and/or methacrylic acid as the acid component and from 0 to 40% of acrylates or methacrylates can be used for controlling fungi and bacteria (European Patent 39,788). This agent has the disadvantage that the copper content is from 0.01 to 10%.

We have found that, because of the higher copper concentration, an agent which, in the form of an aqueous solution, contains more than 10% of copper is more suitable than the known solution for controlling fungi and bacteria. This solution was prepared, for example, by dissolving copper oxide (CuO) in an aqueous solution of the polycarboxylic acid in the presence of ammonia, under atmospheric or superatmospheric pressure and at elevated temperatures. The pressure is, for example, from 1 to 10, preferably from 1.5 to 3, bar, and the temperature is, for example, from 50 to 110° C., preferably from 80 to 100° C., in particular 90° C. The amount of ammonia is more than the equivalent amount, based on the polycarboxylic acid. For example, ammonia is used in an excess of from 10 to 100%.

CuO, which is very sparingly soluble in water, is virtually impossible to dissolve in aqueous poly(meth)acrylic acid or (meth)acrylic acid copolymer solutions at room temperature or elevated temperatures. CuO is also virtually insoluble in ammonia water at room temperature or elevated temperatures under superatmospheric pressure. In aqueous ammonium poly(meth)acrylate solutions too, CuO is only sparingly soluble. However, if ammonia is added in excess, CuO can be dissolved in an amount virtually equivalent to the number of basic units of (meth)acrylic acid in the (co)polymer. Dissolution of the CuO is accelerated by higher ammonia concentrations, and it is therefore advantageous to employ superatmospheric pressure. For a given pressure, the rate of dissolution increases with increasing temperature.

The copper content of the novel agents is restricted by the stoichiometry (not less than 2 moles of monobasic (meth)acrylic acid groups are required per mole of Cu) and by practical considerations, for example the necessity for an easily handled form of the preparations, relatively low viscosity of the liquid preparations and simple preparation of the spray liquor.

CuO in amounts substantially less than the amount equivalent to the number of basic units of (meth)acrylic acid in the (co)polymer is rapidly and completely dissolved. As the equivalent amount of CuO is approached, the residual amount of undissolved CuO increases under otherwise constant conditions, and the reaction time has to be prolonged or the residual solid removed. Although the latter settles out very rapidly, particularly when CuO grades having a high bulk density are used, the costs of separating off the undissolved CuO from the solution make it desirable in practice to achieve as complete dissolution as possible in acceptable reaction times.

The ammonia odor of the agent may be substantially reduced after dissolution of the CuO. Although, as stated above, a high ammonia concentration is advantageous for dissolving the CuO, a major part of the ammonia can be removed after the dissolution procedure, for example by letting down the reactor at elevated temperatures or evaporating or flushing the solution, for example with steam. In this way, the amount of ammonia remaining in the solution can be reduced to far below that corresponding to the stoichiometry of the known tetramminocopper complex. For example, on dissolving the CuO, the molar ammonia/Cu ratio in some cases is substantially higher (up to about 6:1) than the theoretically required amount (4:1). However, the ammonia content of the end product is reduced below that of the diammine complex (2:1) by means of the measures described above, without precipitation or the like occurring. Of course, the properties of the agents change. For example, the viscosity of the agents increases with decreasing ammonia content and settling out of the spray liquor as a result of dilution with water necessitates better stirring in the preparation tank, while the ammonia odor of the agents is substantially reduced. During dissolution of the CuO, the molar ratio of ammonia to Cu is from 6:1 to 4:1. After dissolution of the CuO, the ammonia content of the solution can be reduced, for example to a molar ratio of ammonia to Cu of from 4:1 to 1.9:1.

The long shelf life of the novel agents and the absence of solid deposits during storage at relatively low temperatures are further advantages of the novel agents.

In this way, it is possible to prepare, for example, an agent containing 15% of copper. The copper content of the novel agents is from more than 10 to 25%, for example from 11 to 20%, preferably from 12 to 18%, in particular from 14 to 16%. The biological action of the novel agent on fungi and bacteria is just as good as the action of the known agent when the same amounts of copper are used.

EXAMPLE

In a pressure kettle (nominal pressure 6 bar), 60 kg of the 50% strength aqueous polyacrylic acid having a K value of 25, 15 kg of CuO and 6 kg of water were mixed thoroughly. The air in the kettle was displaced by evacuation or by flushing with ammonia gas. 15 kg of ammonia were then forced into the reactor in the course of 30 minutes, while cooling. The internal temperature of the reactor must not exceed 90° C. When the addition of ammonia is complete, the mixture is kept at 90° C. for a further 4 hours. Thereafter, the kettle is carefully let down (foaming), cooled to 50° C., carefully let down again and evacuated for a short time down to 260 mbar. The solution is then brought to a Cu concentration of 15% by adding water (about 6 kg), and is cooled to 20° C. and discharged. It has a solids content of 46% by weight, a density of 1.3 g/ml at 20° C. and an $NH_3$ content of 12% by weight. The water used is fully demineralized water.

We claim:

1. An agent for controlling fungi and bacteria, based on an aqueous solution of a plant-tolerated copper amine salt of a polymer acid containing from 60 to 100% of acrylic acid or methacrylic acid and from 0 to 40% of an acrylate or methacrylate monomer, said polymer having a measurable K value said solution containing at least 12% by weight copper, which is formed by admixing CuO in an amount sufficient to yield at least 12% weight copper in the final product, with an aqueous solution of said polymer, subjecting said mixture to superatmospheric ammonia gas at a pressure of 1.5 to 3 bars, in the substantial absence of air, wherein said ammonia is present in at least a 10% to 100% excess based on the carboxylic acid equivalent amount of the polymer, for a period of time, and at a temperature sufficient to dissolve the CuO up to the equivalent amount of acid units in said polymer, wherein a solution containing at least 12% values of copper is produced having long term storage stability.

2. The agent of claim 1, wherein said copper content ranges up to 20%.

3. The agent of claim 2, wherein said copper content ranges from 12 to 18%.

4. The agent of claim 3, wherein said copper content ranges form 14 to 16%.

5. A process for producing an agent for controlling fungi and bacteria, based on an aqueous solution of a plant-tolerated copper amine salt of a polymer containing from 60 to 100% of acrylic acid or methacrylic acid and from 0 to 40% of an acrylate or methacrylate monomer, said polymer having a measurable K value, said solution containing at least 12% by weight copper, which is formed by admixing CuO in an amount sufficient to yield at least 12% weight copper in the final product, with an aqueous solution of said polymer, subjecting said mixture to superatmospheric ammonia gas at a pressure of 1.5 to 3 bars, in the absence of air, wherein said ammonia is present in at least a 10% to 100% excess based on the carboxylic acid equivalent amount of the polymer for a period of time, and at a temperature sufficient to dissolve the CuO up to the equivalent amount of acid units in said polymer, wherein a solution containing at least 12% values of copper is produced having long term storage stability.

6. The process of claim 4, wherein said copper content ranges from 11 to 20%.

7. The process of claim 6, wherein said copper content ranges up to 18%.

* * * * *